US011207475B2

(12) United States Patent
Dellaca et al.

(10) Patent No.: US 11,207,475 B2
(45) Date of Patent: Dec. 28, 2021

(54) METHOD AND SYSTEM FOR DELIVERY OF AN AEROSOLIZED MEDICAMENT

(71) Applicant: CHIESI FARMACEUTICI S.P.A, Parma (IT)

(72) Inventors: Raffaele Dellaca, Parma (IT); Ilaria Milesi, Parma (IT)

(73) Assignee: CHIESI FARMACEUTICI S.P.A, Parma (IT)

(*) Notice: Subject to any disclaimer, the term of this patent is extended or adjusted under 35 U.S.C. 154(b) by 318 days.

(21) Appl. No.: 16/319,495

(22) PCT Filed: Jul. 21, 2017

(86) PCT No.: PCT/EP2017/068487
§ 371 (c)(1),
(2) Date: Jan. 22, 2019

(87) PCT Pub. No.: WO2018/019719
PCT Pub. Date: Feb. 1, 2018

(65) Prior Publication Data

US 2021/0069431 A1 Mar. 11, 2021

(30) Foreign Application Priority Data

Jul. 28, 2016 (EP) .................................... 16181786

(51) Int. Cl.
*A61M 11/02* (2006.01)
*A61M 15/00* (2006.01)

(52) U.S. Cl.
CPC ........ *A61M 11/02* (2013.01); *A61M 15/0025* (2014.02); *A61M 15/0035* (2014.02);
(Continued)

(58) Field of Classification Search
CPC ...... A61M 11/00; A61M 11/02; A61M 11/06; A61M 15/00; A61M 15/0028;
(Continued)

(56) References Cited

U.S. PATENT DOCUMENTS 1,998,776 A * 4/1935 Collins .................. A61M 11/02 239/133
3,705,689 A * 12/1972 Lee ........................... B05B 7/24 239/337
(Continued)

FOREIGN PATENT DOCUMENTS

WO WO 93/00951 A1 1/1993
WO WO 2006/108558 A1 10/2006
(Continued)

OTHER PUBLICATIONS

International Search Report dated Aug. 31, 2017 in PCT/EP2017/068487 filed on Jul. 21, 2017.
(Continued)

*Primary Examiner* — Joseph D. Boecker
(74) *Attorney, Agent, or Firm* — Oblon, McClelland, Maier & Neustadt, L.L.P.

(57) ABSTRACT

The method and system according to preferred embodiments of the present invention allows an effective delivery of aerosolized medicament (e.g., a surfactant) to the patient's lungs. According to a preferred embodiment, the method of the present invention provides an efficient delivery of the aerosol medicament (possibly breath synchronized). A glass vial in which medicaments are usually stored and shipped is used directly as a component of the system. Its function in the system is that of an intermittently pressurized chamber that can inject the surfactant into the catheter of the atomizer device. According to a preferred embodiment the delivery can be done in phase with the beginning of each inspiration. The main elements of the system are: a source of com-
(Continued)

pressed gas, the already mentioned medicament vial, a catheter, and optionally means to detect the breathing pattern and a control unit.

11 Claims, 11 Drawing Sheets

(52) U.S. Cl.
CPC . *A61M 15/0091* (2013.01); *A61M 2202/0488* (2013.01); *A61M 2205/273* (2013.01); *A61M 2205/3331* (2013.01); *A61M 2210/1039* (2013.01)

(58) Field of Classification Search
CPC ............ A61M 15/0035; A61M 15/004; A61M 15/0091; A61M 3/0233; A61M 5/155; A61M 16/14; A61J 1/2003; A61J 1/2013
See application file for complete search history.

(56) References Cited

U.S. PATENT DOCUMENTS

| | | | | |
|---|---|---|---|---|
| 3,780,943 | A * | 12/1973 | Lilja | B05B 7/1209 239/8 |
| 4,023,718 | A * | 5/1977 | Forbriger | B05B 7/32 222/399 |
| 4,192,438 | A * | 3/1980 | Foster | A61B 5/0813 222/400.7 |
| 5,458,135 | A | 10/1995 | Patton et al. | |
| 5,775,320 | A | 7/1998 | Patton et al. | |
| 6,138,668 | A | 10/2000 | Patton et al. | |
| 2005/0217668 | A1 | 10/2005 | Figley et al. | |
| 2005/0279349 | A1 | 12/2005 | Patton et al. | |
| 2008/0230053 | A1 | 9/2008 | Kraft et al. | |
| 2008/0269680 | A1* | 10/2008 | Ibranyan | A61M 5/36 604/122 |
| 2009/0000615 | A1 | 1/2009 | Pohlmann et al. | |
| 2009/0211577 | A1 | 8/2009 | Eistetter et al. | |
| 2011/0223116 | A1* | 9/2011 | Century | A61M 15/009 424/45 |
| 2012/0174915 | A1 | 7/2012 | Kraft et al. | |
| 2013/0333695 | A1* | 12/2013 | Dellaca | A61M 16/021 128/200.14 |
| 2014/0290646 | A1* | 10/2014 | Koehler | A61M 11/001 128/200.14 |
| 2015/0034077 | A1 | 2/2015 | Kraft et al. | |
| 2015/0283352 | A1* | 10/2015 | Karkkainen | A61M 16/109 128/203.26 |

FOREIGN PATENT DOCUMENTS

| | | |
|---|---|---|
| WO | WO 2008/094219 A2 | 8/2008 |
| WO | WO 2014/041047 A1 | 3/2014 |

OTHER PUBLICATIONS

European Search Report dated Nov. 3, 2016 in EP16181786.1 filed on Jul. 28, 2016.

* cited by examiner

| | **Air line1** | **Air needle** | **Vial** | **Bubble** | **Surfactant Line** | **Surfactant Needle** | **Surfactant catheter** |
|---|---|---|---|---|---|---|---|
| Inner radius(mm) | 1,0 | 0,25 | | | 1,0 | 0,75 | 0.35 (18cm) + 0.25(0.5 cm) |
| Length(cm) | 50 | 2 | | | 50 | 2 | 18.5 |
| Viscosity(Pas) | 1,86E-5 | 1,86E-5 | | | 0,0103 | 0,0103 | 0,0103 |
| Volume(mL) | | | 3 | 0,1 | | | |

*Fig. 3a*

| | Air line1 | Air needle | Vial | Bubble | Surfactant Line | Surfactant Needle | Surfactant catheter |
|---|---|---|---|---|---|---|---|
| Inner radius(mm) | 1,0 | 0,25 | | | 1,0 | 0,75 | |
| Length(cm) | 50 | 2 | | | 50 | 2 | |
| Viscosity(Pas) | 1,86E-5 | 1,86E-5 | | | 0,0103 | | |
| Volume(mL) | | | 3 | 0,1 | | | |

*Fig. 4a*

| | Air line1 | Air needle | Vial | Bubble | Surfactant Line | Surfactant Needle | Surfactant catheter |
|---|---|---|---|---|---|---|---|
| Inner radius(mm) | 1,5 | 0,25 | | | 1,5 | 0,75 | 0.2 |
| Length(cm) | 50 | 2 | | | 50 | 2 | 10 |
| Viscosity(Pas) | 1,86E-5 | 1,86E-5 | | | 0,0103 | 0,0103 | 0,0103 |
| Volume(mL) | | | 3 | 0,1 | | | |

*Fig. 5a*

| | Air line1 | Air needle | Vial | Bubble | Surfactant Line | Surfactant Needle | Surfactant catheter |
|---|---|---|---|---|---|---|---|
| Inner radius(mm) | 1,5 | 0,25 | | | 1,5 | 0,75 | 0.2 |
| Length(cm) | 50 | 2 | | | 50 | 2 | 10 |
| Viscosity(Pas) | 1,86E-5 | 1,86E-5 | | | 1,86E-5 | 1,86E-5 | 0,0103 |
| Volume(mL) | | | 3 | 0,1 | | | |

*Fig. 6a*

METHOD AND SYSTEM FOR DELIVERY OF AN AEROSOLIZED MEDICAMENT

FIELD OF TECHNOLOGY

The present invention relates to the field of aerosol administration of a medicament and particularly to a method and system for the administration of a pulmonary surfactant by atomization with a breath/synchronized delivery.

BACKGROUND OF THE INVENTION

Administration of medicament in the lungs is often faced with the problem of finding the right balance between the efficacy and the invasiveness of the treatment. The typical approach for delivering medicaments to the lung is based on connecting an aerosol device to the airway opening by means of an interface (for example full face or nasal mask, nasal prongs, mouthpieces, etc.) and allowing the particles generated by the aerosol device to be transported to the lung by the respiratory flow of the patients. However, this approach allows only very modest deposition rates because of several factors, including the waste of the particles generated by the aerosol device during the expiration of the patient. Moreover, the needs of pouring the medicament from the original container/vial to the nebuliser lead to unrecoverable amount of medicament left in the original container as well as in the container of the nebuliser. These factors are limiting the use of aerosol delivery when very expensive or sophisticated medicaments are used.

This problem is particularly evident in preterm neonates (hereinafter the term neonates is used as synonymous of infants.) as they may be affected by nRDS (neonatal Respiratory Distress Syndrome), a lung disease due to generalized immaturity which causes the lack of pulmonary surfactant. For many years, nRDS has been treated by administration of exogenous pulmonary surfactants as bolus through endotracheal instillation to the intubated pre-term neonates kept under mechanical ventilation. Although this treatment is very effective, as proven by the reduced mortality, it presents some drawbacks which are intrinsic to the mechanical ventilation (volu/barotrauma) and to the intubation procedure which is anyway invasive.

Besides, recently, thanks to the introduction in neonatal intensive care of non-invasive ventilation procedures such as early nasal Continuous Positive Airway Pressure (nCPAP), great attention has been paid to find lesser invasive alternative ways for pulmonary surfactant administration.

Therefore, in view of the potential complications associated with intubation and mechanical ventilation, attention has been focused on different approaches of administration of exogenous pulmonary surfactants. Most of the performed studies have been focused on the aerosol lung administration of pulmonary surfactants by means of commercial nebulizers. Commercial nebulizers are placed along the ventilator circuit and the particles produce are conveyed to the patient's mouth through the interface (i.e. nasal mask, prongs) of the ventilator. This nebulizers usually provides very poor deposition rate of surfactant into the lung.

In EP 692273, WO 2013/160129, and WO 2015/059037 another approach has been disclosed, to deliver aerosolized surfactant to the lung based on atomizers. Briefly the terminal part of the device is a catheter placed at the level of the pharynx of the subject producing aerosolized surfactant in loco. The surfactant is conveyed to the atomizing catheter by mean of a volumetric pump, such as an infusion pump.

Interestingly, pre-clinical studies showed that the supraglottic atomization of pulmonary surfactant could provide positive outcomes and large deposition rates compared to standard nebulization (A. Nord et al. "Supraglottic Atomization of Curosurf® via a New Delivery System Allows High Lung Deposition" Proceedings PAS meeting 2015, San Diego; I. Milesi et al. "Atomised Surfactant Improves Oxygenation and Homogeneity of Ventilation in Spontaneously Breathing Preterm Lambs Receiving CPAP" Proceedings PAS meeting 2015, San Diego). The approaches disclosed in EP 692273, WO 2013/160129, and WO 2015/059037 cover a first version of an atomizer device and further improvements that have been mainly introduced to prevent sub-optimal delivering of the medicament due to a poor synchronization of the medicament delivery that should start immediately at the beginning of the inspiration (to take maximal advantage of the inspiratory flow) and stop before the expiration begins, to avoid to deliver medicament when the particles will be exhaled to the atmosphere.

In co-pending PCT application of the same Applicant No. PCT/EP2016/058953 a system is disclosed that allows improving the synchronization of the delivery of the medicament with the existing set-up by implementing a closed-loop control through an adaptive control strategy that compensated the effects of the hydraulic resistance and compliance of the surfactant circuit.

While the system disclosed in PCT/EP2016/058953 provides satisfactory results in most circumstances, in some particular cases the following improvements might be an additional benefit 1) Limiting medicament waste: once the syringe containing the surfactant has been emptied, the medicament (e.g. a surfactant) remaining in the connecting tubes can go wasted. As the connecting tubes cannot be too short to allow proper handling of the patients, a significant amount (0.5 ml or more) can be wasted for each delivery, an improved efficient exploitation of the medicament (e.g. the surfactant) would be welcome;

2) Easiness of use: the medicament must be loaded into the system (e.g. an infusion syringe) and the system must be carefully primed, requiring time from the nurses and exposing to the risk of medicament loss and contamination, therefore a more straightforward and intuitive system operation would be an additional benefit;

3) The high production costs for the single-use, disposable kit comprising e.g. a glass syringe and pressure sensors can limit a broad diffusion of this method. A reduced cost of the disposable part of the system would be much appreciated.

The above improvements would be desirable, independently form the delivery method used in the system.

For all these reasons, an improved method and system for administering an aerosolized medicament (e.g. an exogenous pulmonary surfactant) would be greatly appreciated.

OBJECTS OF THE INVENTION

It is an object of the present invention to overcome at least some of the problems associated with the prior art.

SUMMARY OF THE INVENTION

The present invention provides a method and system as set out in the accompanying claims.

According to one aspect of the present invention, we provide a system for delivering an aerosolized medicament to spontaneously breathing patients, comprising: a source of compressed gas; a disposable vial partly filled with a liquid medicament; an assembly adapted to be connected to the disposable vial comprising: a first channel conveying the compressed gas to the portion of the vial not containing the liquid medicament; a second channel for conveying the liquid medicament from the vial to the patients' lungs; wherein, in operation, the compressed gas generates a controllable pressure in the vial which results in the liquid medicament being delivered to the patients' lungs. Preferably the disposable vial includes: closing means; an input needle passing across the closing means, the input needle connecting the first channel with the vial; an output needle passing through the closing means, the output needle connecting the vial with the second channel. In a preferred embodiment of the present invention the length and the positioning of the input needle is selected so that, in operation, the end of the needle inside the disposable vial is positioned in the portion of the vial not containing the liquid medicament, while the length and the positioning of the output needle is selected so that, in operation, all the liquid medicament can flow through the output needle. Preferably closing means include a rubber cap or any other resilient material which ensure proper sealing to the vial even after perforation by the needles.

The medicament can include a pulmonary surfactant.

In a preferred embodiment the disposable vial is made of glass.

According to a second aspect of the present invention, a vial is provided which is adapted to be used in the system defined above.

Also according to a further aspect of the present invention, a pulmonary surfactant is provided to be used as medicament with the system defined above.

In a preferred embodiment of the present invention breathing detecting means includes pressure detective means, for measuring a value indicative of the pressure in the patient pharyngeal cavity, such value being used to determine whether the patient is in an inspiration or in an expiration phase.

The aerosol medicament is a propellant-free pharmaceutical formulation in form of aqueous solution or suspension. For example, the medicament can comprise an exogenous pulmonary surfactant, possibly selected from the group consisting of modified natural pulmonary surfactants (e.g. poractant alfa), artificial surfactants, and reconstituted surfactants.

Also, in a preferred embodiment, the pressurized gas includes air, oxygen or a mixture of the two.

A still further aspect of the present invention provides a computer program for controlling the above described method.

In a further aspect of the invention a method is provided for the prophylaxis and/or treatment of Respiratory Distress Syndrome or related diseases, said method comprising administering, with the above defined device, aerosolized medicaments to the lungs of a patient in need of such treatment.

Also included in the present invention is a kit including all disposable part of the system. In a preferred embodiment the kit includes the vial and the second channel. In a further embodiment the kit also includes the first channel and the assembly for connecting the first and second channel to the vial.

The method and system of the present invention provides an efficient delivery of medicaments (e.g. pulmonary surfactant) by nebulization or atomization, obtaining several advantages, including the use of components which are already familiar to the hospital personnel, e.g. catheters; all the part in contact with the pulmonary surfactant and the patient are low cost, disposable and largely pre-assembled, granting for hygienically and safe treatments, which is particularly important when the patient is a pre-term neonate or a fragile severe children or adult. Additional advantages are:

- Reduction of medicament waste;
- Simple, robust and less expensive atomizing devices;
- Fast time to set up the system by the operator without requiring special skills and training;
- Low production costs for the single-use disposable kit.
- Low risks of contamination of the medicament as no pouring from the original container is needed.

BRIEF DESCRIPTION OF THE DRAWINGS

Reference will now be made, by way of example, to the accompanying drawings, in which.

DEFINITIONS

Figure 1:
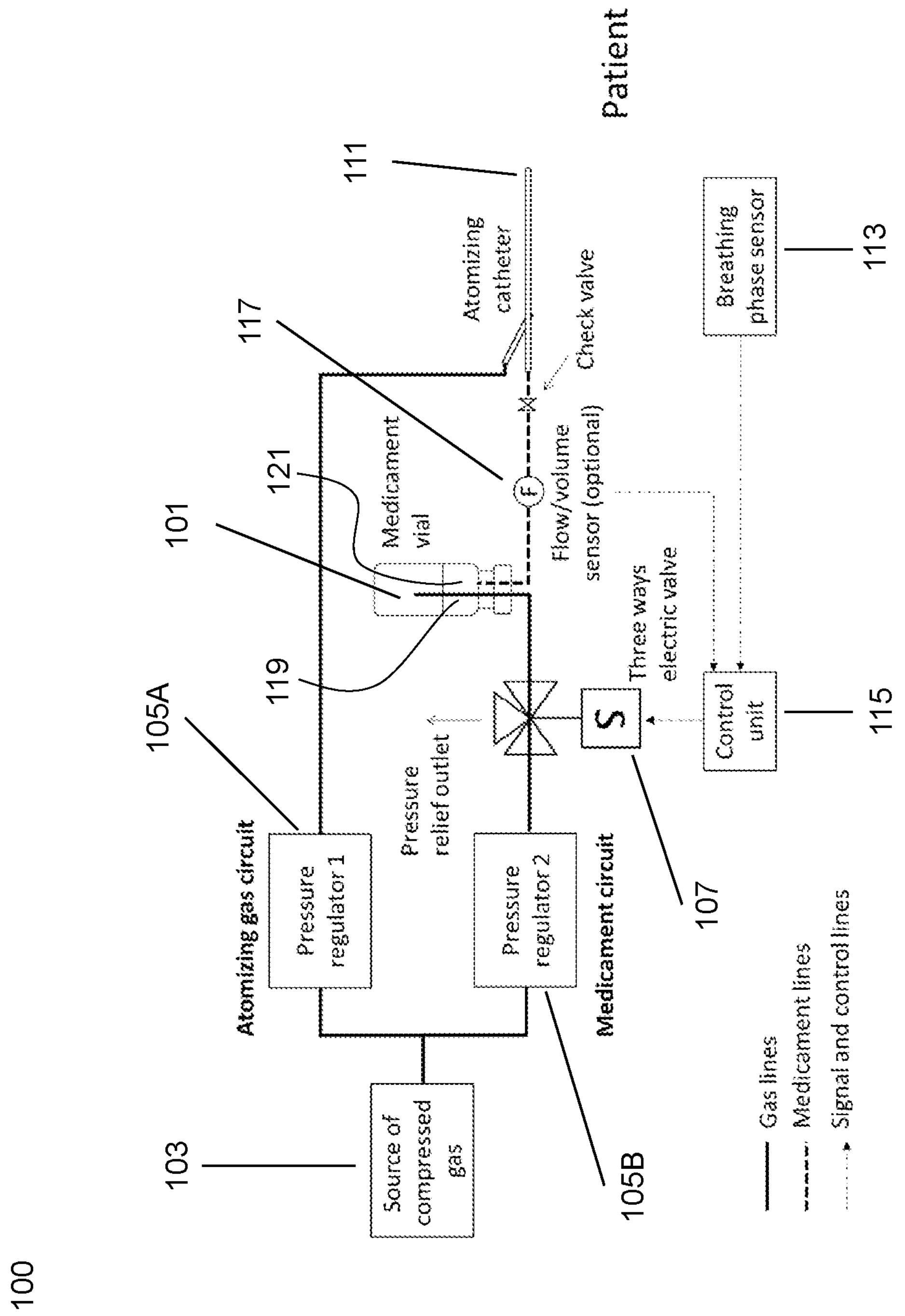
FIG. 1 is a schematic diagram of one of the possible systems of the prior art.

The terms "neonates" and "newborns" are used as synonymous to identify very young patients, including pre-term babies having a gestational age of 24 to 36 weeks, more particularly between 26 and 32 weeks.

With the term "pulmonary surfactant" it is meant an exogenous pulmonary surfactant administered to the lungs that could belong to one of the following classes:

i) "modified natural" pulmonary surfactants which are lipid extracts of minced mammalian lung or lung lavage. These preparations have variable amounts of SP-B and SP-C proteins and, depending on the method of extraction, may contain non-pulmonary surfactant lipids, proteins or other components. Some of the modified natural pulmonary surfactants present on the market, like Survanta™ are spiked with synthetic components such as tripalmitin, dipalmitoylphosphatidylcholine and palmitic acid.

ii) "artificial" pulmonary surfactants which are simply mixtures of synthetic compounds, primarily phospholipids and other lipids that are formulated to mimic the lipid composition and behavior of natural pulmonary surfactant. They are devoid of pulmonary surfactant proteins;

iii) "reconstituted" pulmonary surfactants which are artificial pulmonary surfactants to which have been added pulmonary surfactant proteins/peptides isolated from animals or proteins/peptides manufactured through recombinant technology such as those described in WO 95/32992 or synthetic pulmonary surfactant protein analogues such as those described in WO 89/06657, WO 92/22315, and WO 00/47623.

The term "non-invasive ventilation (NIV) procedure defines a ventilation modality that supports breathing without the need for intubation.

The term "vial", as used in the present description, is intended to include containers of different shape, made of glass and/or any other rigid material.

DETAILED DESCRIPTION OF PREFERRED EMBODIMENTS

With reference to the accompanying figures an implementation of the method and system according to a preferred embodiment of the present invention is illustrated. In the example here discussed we address the problem of optimising the delivering of aerosol medicament to a patient.

To administer the medicament, atomizer devices such as those disclosed in EP 692273, WO 2013/160129, and WO 2015/059037 could be advantageously utilised, preferably the devices for supra-glottic administration such as those disclosed in WO 2013/160129, and WO 2015/059037.

In an alternative embodiment, nebulizers such as vibrating mesh devices (such as Aerogen Pro (Aerogen INC, USA) or Akita™ (Activaero GmbH, Germany)) or jet nebulizers could be employed. Those skilled in the art will appreciate that several different solutions could be used instead.

However, the method and system according to the invention could also be used in combination with a catheter for the delivery of a medicament to spontaneously breathing patients.

In a particular embodiment, a catheter for minimally invasive endotracheal administration of a pulmonary surfactant could be utilized, for example according to procedure disclosed in WO 2008/148469 or in Dargaville Pa. et al Arch Dis Fetal Neonatal Ed 2013, 98(2), 122-126. Said catheter should have a diameter equal to or lower than 5 French (hereinafter Fr) corresponding to about 1.66 mm (1 French corresponds to ⅓ mm). Advantageously the diameter shall be comprised between 2.0 and 5.0 Fr. Preferred diameters would be 3.5, 4.0 and 5.0 Fr.

To act as a catheter according to the invention, any gastric or nasogastric tube, arterial or suction catheter of common use in hospitals can be utilized. It may be made of any material, preferably of polyurethane or silicone, and could have a length comprised from 10 to 35 cm, preferably of 15 cm or 30 cm.

The medicament is administered as a propellant-free aqueous solution or suspension in a sterile pharmaceutically acceptable aqueous medium, preferably in a buffered physiological saline (0.9% w/v sodium chloride) aqueous solution.

Its concentration shall be properly adjusted by the skilled person in the art. Advantageously, a pulmonary surfactant (e.g. poractant alfa, commercially available as Curosurf® from Chiesi Farmaceutici SpA) could be administered to e.g. a preterm neonate.

However, any pulmonary surfactant currently in use, or hereafter developed for use in respiratory distress system and other pulmonary conditions could be suitable for use in the present invention. These include modified natural, artificial and reconstituted pulmonary surfactants (PS).

Current modified natural pulmonary surfactants include, but are not limited to, bovine lipid pulmonary surfactant (BLES™, BLES Biochemicals, Inc. London, Ont), calfactant (Infasurf™, Forest Pharmaceuticals, St. Louis, Mo.), bovactant (Alveofact™, Thomae, Germany), bovine pulmonary surfactant (Pulmonary surfactant TA™, Tokyo Tanabe, Japan), poractant alfa (Curosurf®, Chiesi Farmaceutici SpA, Parma, Italy), and beractant (Survanta™, Abbott Laboratories, Inc., Abbott Park, Ill.)

Examples of artificial surfactants include, but are not limited to, pumactant (Alec™, Britannia Pharmaceuticals, UK), and colfosceril palmitate (Exosurf™, GlaxoSmithKline, plc, Middlesex).

Examples of reconstituted surfactants include, but are not limited to, lucinactant (Surfaxin™, Discovery Laboratories, Inc., Warrington, Pa.) and the product having the composition disclosed in Table 2 of Example 2 of WO2010/139442. Preferably, the pulmonary surfactant is a modified natural surfactant or a reconstituted surfactant. More preferably the pulmonary surfactant is poractant alfa (Curosurf®). In another preferred embodiment, the reconstituted surfactant has composition disclosed in WO2010/139442 (see Table 2 of Example 2 of WO2010/139442).

Advantageously, the concentration of the surfactant might be comprised between 2 and 160 mg/ml, preferably between 10 and 100 mg/ml, more preferably between 40 and 80 mg/ml.

The dose of the pulmonary surfactant to be administered varies with the size and age of the patient, as well as with the severity of the patient's condition. Those of skill in the relevant art will be readily able to determine these factors and to adjust the dosage accordingly.

Other active ingredients could advantageously be comprised in the medicament according to the invention including small chemical entities, macromolecules such as proteins, peptides, oligopeptides, polypeptides, polyamino acids nucleic acid, polynucleotides, oligo-nucleotides and high molecular weight polysaccharides, and mesenchimal stem cells derived from any tissue, in particular from a neonate tissue. In a particular embodiment, small chemical entities include those currently used for the prevention and/or treatment of neonatal respiratory diseases, for example inhaled corticosteroids such as beclometasone dipropionate and budesonide.

Advantageously, the method and system according to the invention are utilized for administering by aerosol a medicament to spontaneously breathing patients, preferably neonates, more preferably pre-term neonates to which non-invasive respiratory support of mechanical ventilation such as nasal Continuous Positive Airway Pressure (nCPAP) or high flow nasal cannula (HFNC) or also non-invasive mechanical ventilation (NIV) are applied. Moreover, as the method and system according to the invention do not interfere with the respiratory support device, the invention can be used in combination to whichever non-invasive respiratory device.

FIG. 1 shows a block diagram of a preferred embodiment 100 of the present invention. The glass vial 101 in which medicaments are usually stored and shipped is used directly as a component of the system. Its function in the system is that of an intermittently pressurized chamber that can inject the surfactant into the catheter (e.g. an atomizing catheter). In a preferred embodiment of the present invention, the delivery is performed in phase with the beginning of each inspiration. In a preferred embodiment the vial 101 is made of glass and has a capacity preferably equal to or less than 20 ml, more preferably equal to or less than 12 ml and even more preferably equal to or less than 6 ml.

The main elements of the system 100 are: a source of compressed gas 103 (either medical gas wall plugs or compressors), two pressure regulators 105*a* and 105*b* arranged to provide two gas sources at independent levels of pressure, a three-way solenoid valve 107, the already mentioned medicament vial 101, a check valve 109, a medicament delivering catheter 111, means 113 to detect the breathing pattern and a control unit 115. As an option, a flow/volume sensor 117 can be added to the system to measure the amount of medicament effectively delivered.

These elements are organized into two different circuits: the pressurized gas circuit and the medicament circuit. When in operation, the two circuits begin from the source of compressed breathable-grade gas 103 and, after having followed different and separate paths, join together at the entrance of the delivering catheter 111.

The pressurised gas line provides the proper gas flow to the delivering catheter 111 for delivering the medicament, e.g. by atomization of the medicament (for instance 0.1-0.8 LPM). The first pressure regulator 105*a* can be used to preset the flow rate. Specific pressure levels for every catheter and circuit is not needed because of 1) the good reproducibility of the geometry of the gas lumen of the catheter and the gas circuit (that makes the variability of the pressure-flow relationship very limited) and 2) the relatively low sensitivity of the whole system to changes in this pressure.

The pressure of the gas from the source is also adjusted to a second targeted value by means of the second pressure regulator 105*b*. This pressurized gas is then delivered to the internal gas volume of the medicament vial by means of a three ways solenoid valve 107. In a preferred embodiment the vial 101 is provided with a perforable closure (e.g. a rubber cup): in this case a needle 119 is adapted to puncture the vial rubber cup to reach the internal space free from the medicament. The medicament flows out of the vial towards a second needle 121 of different length and a check valve to enter the catheter (e.g. an atomizing catheter). The length of the two needles are designed to allow the gas to be injected where there is already gas in the vial and to have the liquid medicament being extracted out from the vial. The dimensions of the needles depend on the dimension of the vial and its position relative to the gravity vector (top-up or upside down). There are two different options according to the position of the vial in operation: if the vial is to be positioned upside down, i.e. the free space is at the bottom of the vial, the “input” needle inserting pressurized gas will be long enough to reach the free space, while the “output” needle collecting the medicament will be short enough to collect all the possible medicament. If the vial is supposed to be positioned top-up, in which case the free space is next to the opening of the vial, the “input” needle must be short enough to end up in the free space, while the output needle must be long enough to collect as much medicament as possible. In the present example we have considered the upside-down position of the vial.

In more details, when the gas in the vial 101 is pressurized by activating the three-way valve 107, the pressure is immediately transferred to the medicament inside the vial and the pressurized medicament flows into the medicament circuit toward the catheter (e.g. an atomizing catheter) 111. As the time needed for the transmission of the pressure from the gas to the medicament is almost negligible, it is possible to obtain very fast rising time for surfactant atomization at the catheter’s tip. Similarly, when the vial is depressurized by deactivating the three way valve 107, which results in connecting the inner of the vial to the atmosphere through the pressure relief outlet, the pressure of the medicament is rapidly relieved too, therefore the medicament flow stops almost immediately providing very short stopping time.

Targeted surfactant flow rate is around 1.2 ml/min during atomization, leading to the need of a pressure into the vial ranging from 20 to 200 $cmH_2O$ depending on the hydraulic resistance of the catheter (e.g. an atomizing catheter).

Even if the transmission of the pressure from the gas inside the vial to the medicament is extremely fast, the pressurization and the depressurization of the gas within the vial require mass transport of gas in and out from the vial. Those skilled in the art will appreciate that a prompt pressurization and depressurization of the vial can be obtained with a proper design of the pneumatic characteristics of the gas tubing and connections in the medicament circuit. In particular, the gas inside the vial acts as a compliance while the inlet of the vial, which is a needle (more details will be provided later) acts a resistance (inertance of the system may be neglected because of the very low density of the air). Therefore, the time constant of the system is defined by the coupling of resistance and compliance, which implies a peculiar design of the needle to make the resistance as low as possible being the compliance of the vial (due to the air inside the vial) fixed. However, the skilled person will find no difficulties in obtaining the appropriate values of resistance needed by the pressurizing circuits with standard tubing and connections.

When the vial is depressurized, the medicament in the medicament line could be partially reinjected into the vial making the delivery less effective. In order to avoid this, a check valve (which in a preferred embodiment is disposable) can be added on the medicament line just at the inlet of the catheter (e.g. an atomizing catheter) to prevent the medicament from flowing backwards from the catheter to the vial.

When it is necessary to deliver a precise amount of medicament different from the full load of the vial or when is desirable to provide a continuous monitoring of the delivery of the medicament during the treatment, an optional flow sensor 117 able to measure the amount of medicament flowing through the medicament line can be added to the system.

As mentioned above the system according to preferred embodiments the present invention provides several advantages compared to the known systems. The advantages include a major improvement of timing associated to the delivery of surfactant synchronized with the breathing phase; the system is also very simple to use as no difficult or sensitive priming procedures of the disposable circuits are needed. Furthermore, the waste of the medicament is reduced to the minimum, since it is possible to deliver also the medicament (e.g. surfactant) “trapped” into the tubes and lines. The cost of production of the device is also very low thanks to the use of standard widely-available low-cost components. At the same time, also production costs and complexity of the disposable kits are largely reduced, as no glass syringes, piezo-electric vibrating meshes, pressure sensors ore other complex components are required for the disposable equipment. The disposable kit is made only of plastic and eventually metal parts and will comprise the needles for connecting the vial, the connecting tubes, the catheter (e.g. an atomizing catheter), the interface and a commercially available disposable check valve. The kit can be easily pre-assembled, sterilized and delivered ready to use.

Laboratory tests and mathematical simulations have been performed to validate the performances of the system.

The results of mathematical simulations are presented here below presented followed by the results of in vitro testing.

Modelling Simulations

It is possible to model the system by using lump parameters linear model. For the following simulations, a target surfactant flow rate of 1.2 mL/min during the delivery phase has been considered.

Figure 2:
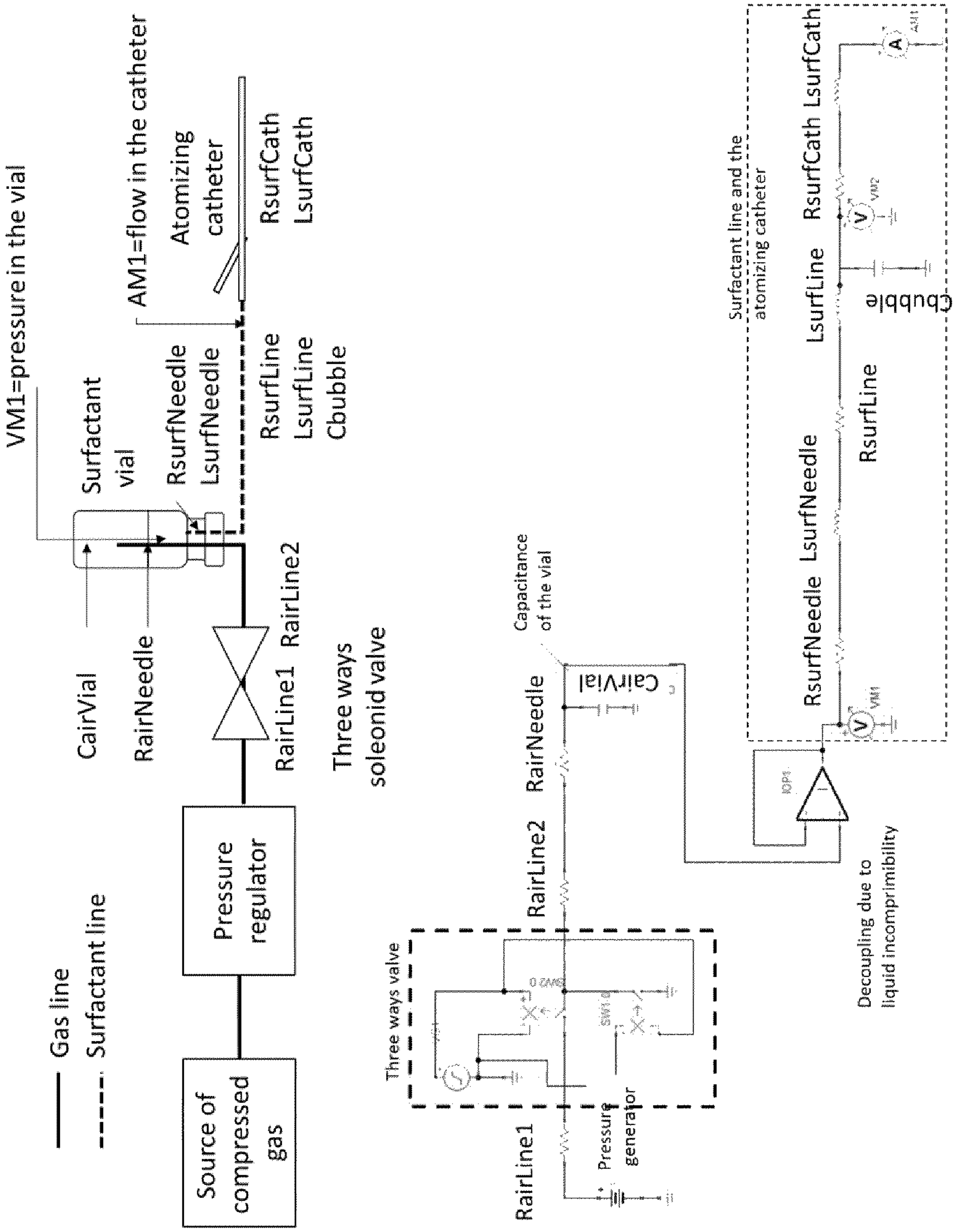
FIG. 2 shows a schematic representation of a system according to a preferred embodiment of the present invention.

FIG. 2 shows a general diagram of the simulated system, physical components are reported together with their analog representation.

In the following simulations, the geometrical dimensions of each component are reported together with the pressure measured at the level of the vial (VM1), the pressure measured at the inlet of the catheter (VM2) and the flow generated in the medicament catheter (AM1) as responses to step gas pressure changes.

Several cases have been tested, each of them is representative for a different geometry of the catheter (e.g. an atomizing catheter), less or more challenging in terms of mechanical resistance.

Case1: Atomizing Catheter (Surfactant Lumen ID=0.7 mm)

Table 1 as represented in FIG. 3*a* reports the dimensions of the elements composing the system. The parts are named as per FIG. 2.

Figure 3B:
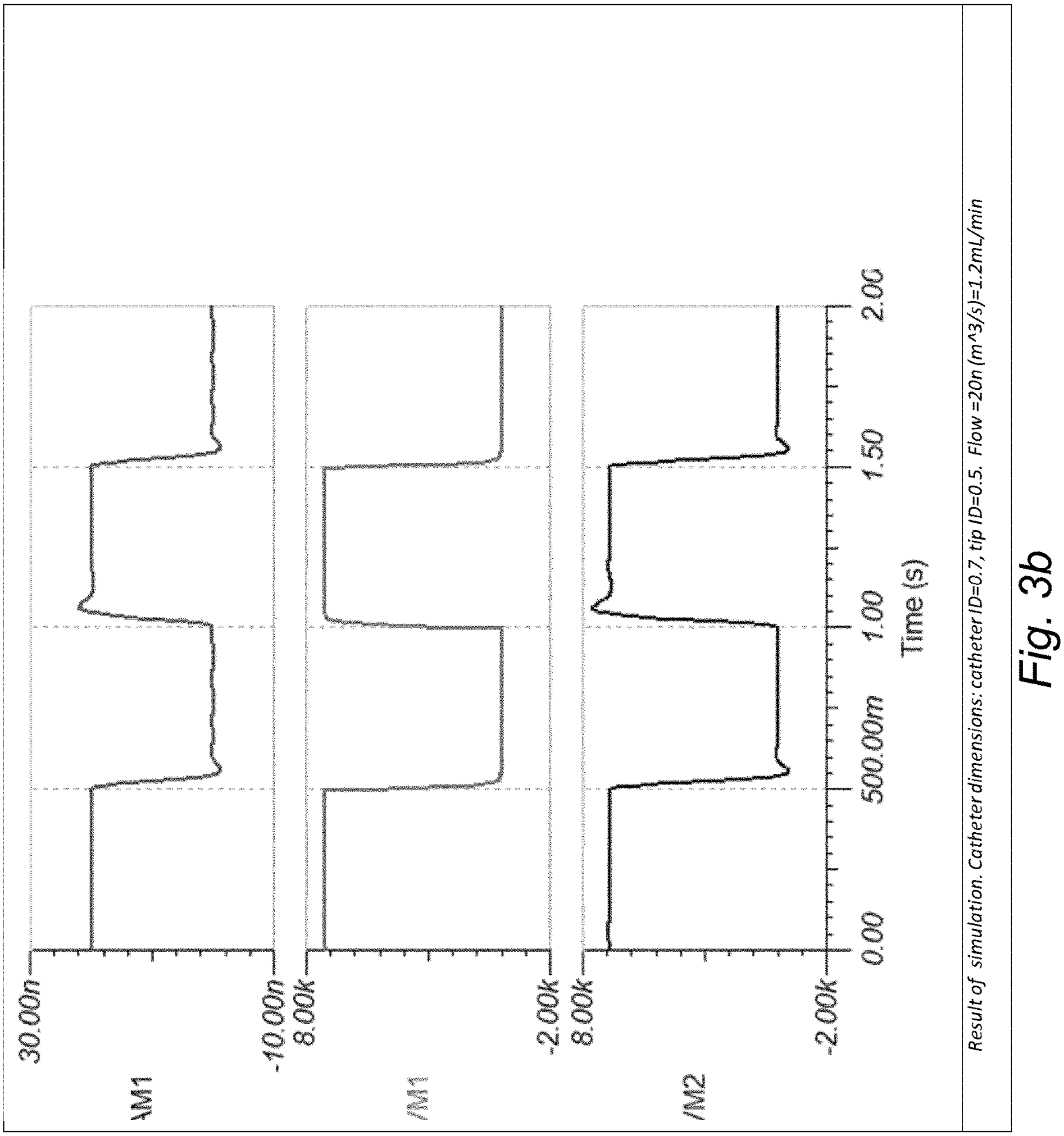
FIGS. 3-6 show the breathe diagram of 4 different cases discussed below.

The result is shown in FIG. 3*b*. It is worthwhile to notice that the rising time (from 10 to 90% of the target medicament flow) is really short (27 ms) and the system looks just slightly underdamped.

Case2: Atomizing Catheter (Surfactant Lumen ID=0.22 mm)

Table 2 as represented in FIG. 4*a* reports the dimensions of the elements of the system. The parts are named as per FIG. 2.

Figure 4B:
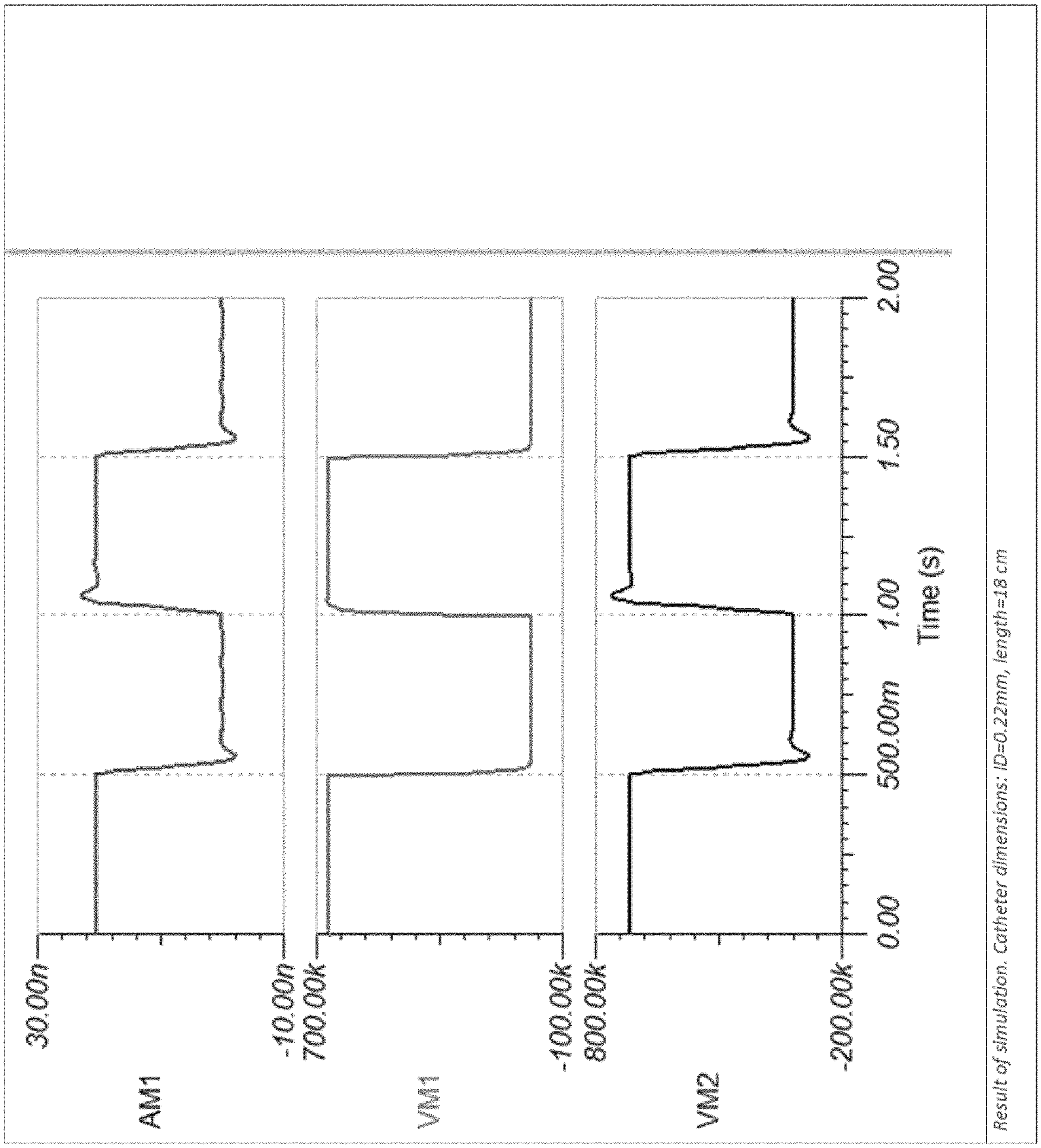

The results are shown in FIG. 4*b*. It is worthwhile to notice that the rising time is really short (35 ms) although the resistance of the catheter is extremely high. In this configuration, the pressure needed to deliver the desired flow is very high (6.45 Bar). However, these conditions are considered only as extreme situation as the resistance of the medicament line is more than 100 times bigger than the previous case and not realistic for clinical applications.

Case3: Atomizing Catheter (Surfactant Lumen ID=0.4)

In this case a catheter with intermediate characteristics compared to the previous two cases has been considered.

Table 3 as represented in FIG. 5*a* reports the physical dimensions of the elements composing the system. The parts are named as per FIG. 2.

Figure 5B:
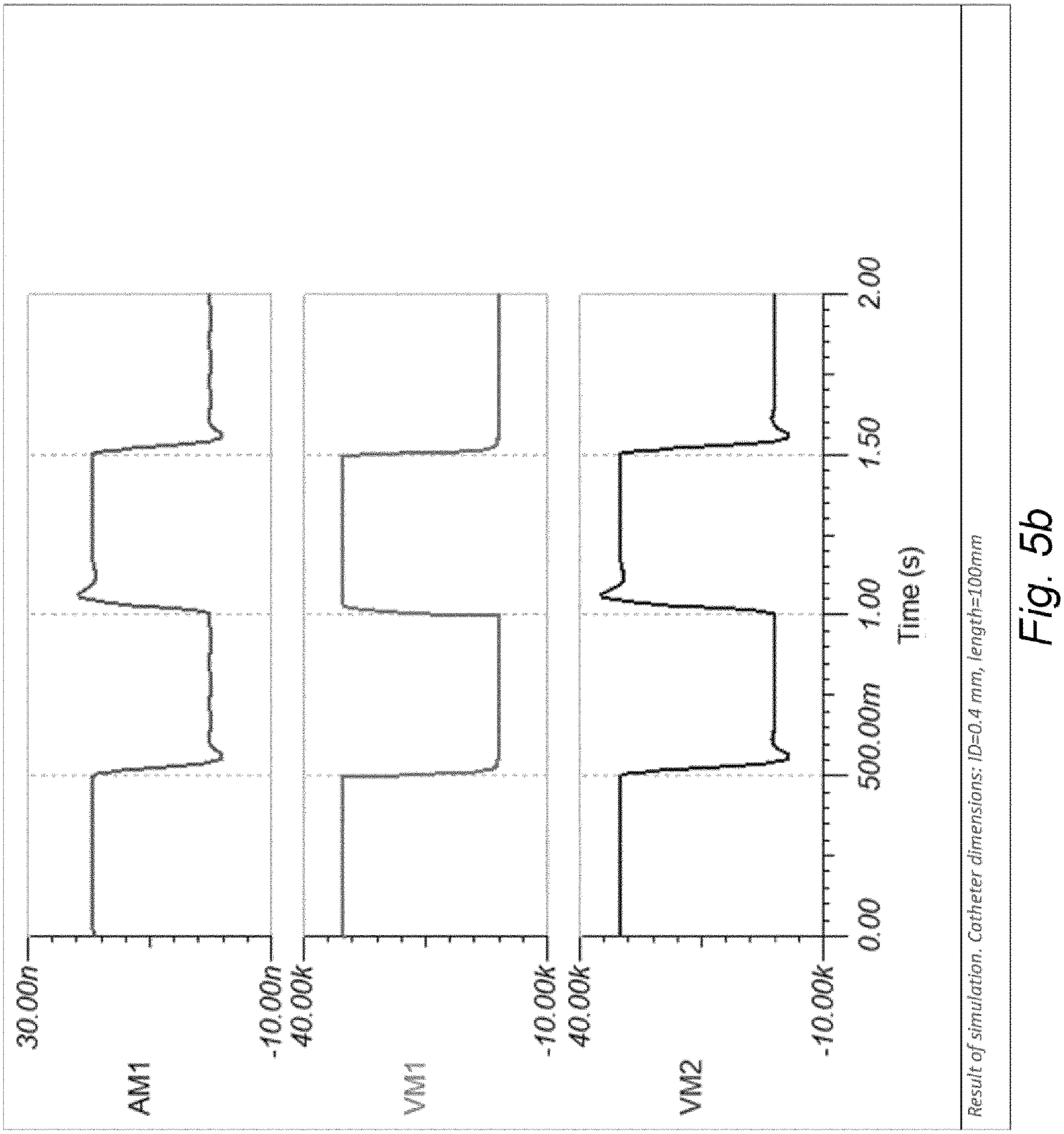

The results are shown in FIG. 5*b*. It is worthwhile to notice that the rising time is really short (25 ms). Moreover, the pressure level needed to pressurize the vial is only 0.3 bar, which is much less than in the case above and suitable for clinical applications.

Case4: Atomizing Catheter (Surfactant Lumen ID=0.4) and Empty Surfactant Line

Given the good performances of the cases above, we investigated what happens when the surfactant remaining in the surfactant line is delivered as well. In this simulation, the scenario in which the surfactant line is totally filled with air is explored. In this condition the medicament line offers a much lower resistance (10^-4 because of different density and viscosity of air compared to surfactant) but greater compliance than surfactant (which is uncompressible unless for the bubbles inside).

Table 4 as represented in FIG. 6*a* reports the physical dimensions of the elements composing the system. The parts are named as per FIG. 2.

Figure 6B:
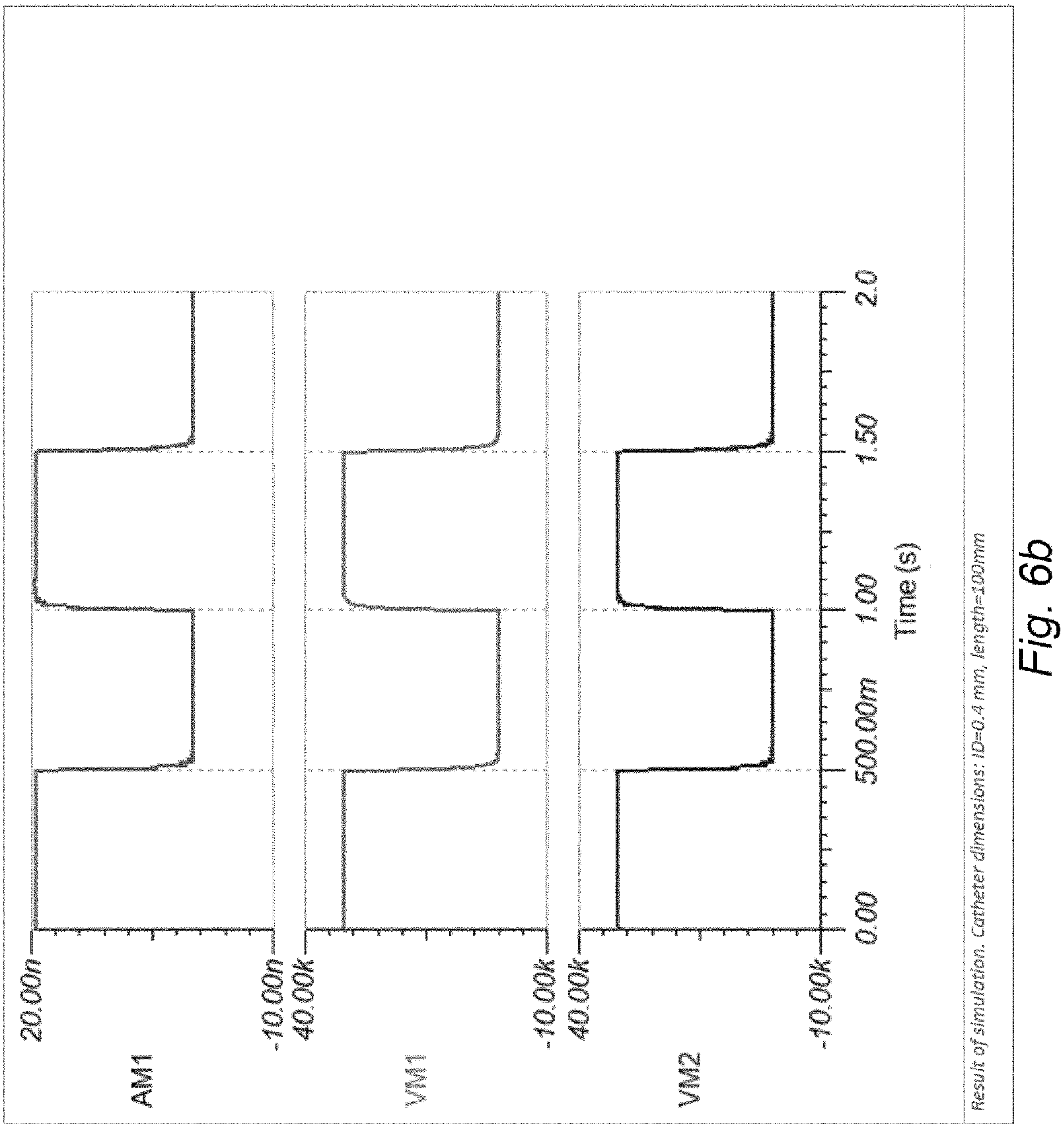

The results are shown in FIG. 6*b*, The rising time is still extremely fast. Since the resistance is dominated by the catheter, there are no significant changes in the pressure needed to atomize the medicament, which is still approximately 0.3 Bar.

In Vitro Test

In order to test the efficacy of the invention, an in vitro test was performed using the preferred embodiment described above. A device disclosed in WO 2015/059037 was used with the geometrical characteristics reported in simulation case 1.

In order to assess the rising and falling time of the surfactant flowing into the atomising catheter, a pressure sensor has been inserted along the surfactant line at the inlet of the atomising catheter.

As the tip of the atomizing catheter is in the air, it is exposed at a pressure corresponding to the Atmospheric pressure, therefore the pressure drop across the atomizing catheter is equal to the pressure measured by the pressure sensor at the inlet of the catheter.

Being the flow through the catheter proportional to the pressure drop, by means of a preliminary calibration it has been possible to estimate the medicament flow through the atomizing catheter from the pressure assessed by the pressure sensor at the inlet of the atomizing catheter.

For this experiment, the pressure regulator for the pressurizing the vial was set to 30 $cmH_2O$. The surfactant line was automatically primed by opening the solenoid valve which pressurizes the vial until the surfactant reached the tip of the atomizing catheter. After priming was completed, a square wave signal at 0.5 Hz has been used to trigger the solenoid valve simulating a symmetric breathing at 30 breaths per minute with an inspiratory time of 1 s.

Figure 7:
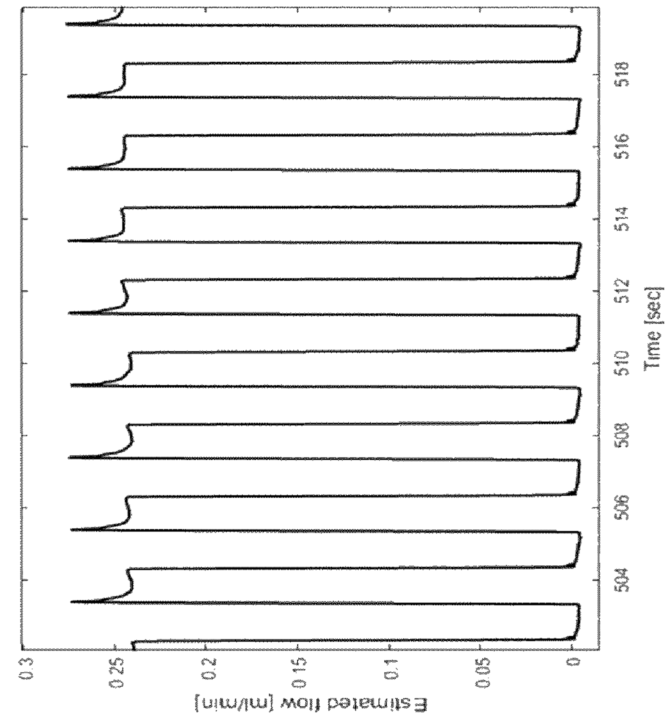
FIG. 7 shows the results according to a specific example test.

The surfactant flow tracing is reported in FIG. 7. The resulting rising and falling time of the surfactant flow are only 50 and 60 ms, respectively.

The invention claimed is:

1. A system purposefully arranged for delivering an aerosolized medicament to a spontaneously breathing patient, comprising:

a source of compressed gas;

a disposable vial partly filled with a liquid medicament;

an assembly adapted to be connected to the disposable vial comprising:

a first channel for conveying the compressed gas to a portion of the disposable vial not containing the liquid medicament; and a second channel for conveying the liquid medicament from the disposable vial to the patient's lungs; and means to detect the patient's breath, wherein, in operation, the compressed gas generates a controllable pressure in the disposable vial which results in the liquid medicament being delivered to the patient's lungs, and wherein the disposable vial includes:

closing means;

an input needle passing across the closing means, the input needle connecting the first channel with the disposable vial; and an output needle passing through the closing means, the output needle connecting the disposable vial with the second channel.

2. The system of claim 1, wherein a length and a positioning of the input needle is selected so that, in operation, an end of the input needle inside the disposable vial is positioned in the portion of the disposable vial not containing the liquid medicament, and a length and a positioning of the output needle is selected so that, in operation, all the liquid medicament can flow through the output needle.

3. The system of claim 1, wherein the closing means includes a rubber cap or a cap of a resilient material suitable to ensure hydraulic seal to the disposable vial even after the input needle and the output needle are in place.

4. The system of claim 1, wherein the means to detect patient's breath includes pressure detective means, for measuring a value indicative of a pressure in the patient's pharyngeal cavity, such value being used to determine whether the patient is in an inspiration phase or in an expiration phase.

5. The system of claim 1, wherein the liquid medicament is delivered only when the patient is in the inspiration phase.

6. The system of claim 1, wherein the liquid medicament includes a pulmonary surfactant.

7. The system of claim 1, further including an atomizing device.

8. The system of claim 1, further including a nebulizing device.

9. The system of claim 1, wherein the disposable vial is made of glass.

10. The system of claim 1, wherein, in the closing means, the input needle is spaced apart from the output needle.

11. The system of claim 1, wherein lengths of the input needle and the output needle are selected to allow the compressed gas to be injected where there is already gas in the disposable vial while the liquid medicament is extracted out from the vial.

* * * * *